United States Patent [19]
Tanaka et al.

[11] 4,281,674
[45] Aug. 4, 1981

[54] APPARATUS FOR CLEANING ENDOSCOPE

[75] Inventors: Masahiro Tanaka, Tokyo; Katunaga Konoshima, Hachioji, both of Japan

[73] Assignee: Olympus Optical Company, Ltd., Japan

[21] Appl. No.: 70,622

[22] Filed: Aug. 29, 1979

[30] Foreign Application Priority Data

Nov. 27, 1978 [JP] Japan .................. 53/146301

[51] Int. Cl.³ .................................... B08B 3/02
[52] U.S. Cl. ....................... 134/95; 134/96; 134/103; 134/170; 134/171
[58] Field of Search .................. 134/95-96, 134/98-101, 103, 169 R, 169 C, 170-171, 94, 153, 180-181, 199

[56] References Cited

U.S. PATENT DOCUMENTS

| | | | |
|---|---|---|---|
| 2,963,029 | 12/1960 | Bock | 134/95 X |
| 3,173,433 | 3/1965 | Wynne et al. | 134/95 X |
| 3,417,763 | 12/1968 | Fjermestad et al. | 134/103 X |
| 3,587,597 | 6/1971 | Courtney et al. | 134/96 X |
| 3,620,232 | 11/1971 | D'Angelo | 134/96 X |
| 4,064,886 | 12/1977 | Heckele | 134/95 |

FOREIGN PATENT DOCUMENTS

| | | | |
|---|---|---|---|
| 51-25493 | 2/1976 | Japan | 134/199 |
| 51-140590 | 11/1976 | Japan | 134/199 |
| 52-87066 | 6/1977 | Japan | 134/199 |

*Primary Examiner*—Robert L. Bleutge
*Attorney, Agent, or Firm*—Ostrolenk, Faber, Gerb & Soffen

[57] ABSTRACT

An apparatus for cleaning an endoscope includes a return system for returning used sterilizer a from a drain port of a rinse basin to the reservoir vessel containing the liquid sterilizer medium, via a return tube, which may contain an electromagnetic valve. The apparatus also includes a drain tube for discharging waste liquid through the drain port; the drain tube may include an electromagnetic valve. In this manner, a liquid sterilizer which is discharged from the drain port of the rinse basin may be returned to the reservoir vessel through the return tube, permitting its repeated use as long as the liquid sterilizer remains effective.

7 Claims, 3 Drawing Figures

(A),(C),(G) CLEANING WITH WATER
(B) CLEANING WITH DETERGENT
(D),(F) QUIESCENT PERIOD
(E) CLEANING WITH STERILIZER
(H) DRYING

APPARATUS FOR CLEANING ENDOSCOPE

BACKGROUND OF THE INVENTION

The invention relates to an apparatus for cleaning an endoscope, and more particularly, to an apparatus for cleaning a portion of an endoscope which has been inserted into the coeloma and used therein.

As is well recognized, an endoscope which is used for the medical purpose of obtaining an observation of an affected area within the coeloma comprises an elongate flexible tube internally containing an observation system and an illumination optical system each formed of a bundle of optical fibres and also containing a channel utilized to feed air or a liquid to the coeloma, to withdraw a coeliac fluid therefrom or to insert forceps, and an operating end which is located outside the coeloma to permit various manual operations. When the distal end of the endoscope is withdrawn from the coeloma after the termination of diagnosis or therapy with the endoscope, it has coeliac fluid, blood and other contaminants attached thereto. Hence, it is necessary to clean and sterilize the distal end of the endoscope which has been inserted into the coeloma before using it again.

A conventional cleaning apparatus used for this purpose comprises a rinse basin which is adapted to receive a distal end or an inner end of an endoscope therein and toward which water, a detergent solution or a sterilizing solution is directed in sequence, thus cleaning the endoscope. When a sterilizing solution is to be sprayed, a sterilizing liquid is mixed with water to establish a given concentration before it is sprayed. After each sterilizing operation, the sterilizing solution is disposed of. Consequently, a substantial amount of sterilizing solution is discharged from the cleaning apparatus, to increasing the consumption of the expensive sterilizing solution. This also requires frequent recharging thereof, resulting in increased overall operating cost of the apparatus. A sterilizing solution generally remains effective for a given period of time. For example, glutaraldehyde remains effective for two weeks. Hence, it is wasteful to dispose of the sterilizing solution after each sterilizing operation.

SUMMARY OF THE INVENTION

It is an object of the invention to provide an apparatus for cleaning an endoscope in which a sterilizing solution which is discharged through a drain port of a rinse basin is returned to a storage vessel through a circulation path to permit its reintroduction into the rinse basin and its repeated use so long as the solution remains effective.

It is another object of the invention to provide an apparatus for cleaning an endoscope in which the return of the sterilizing solution is achieved in an optimum manner.

According to the invention, return of the sterilizing solution, ones used, to the rinse basin in order to enable its repeated use substantially reduces the consumption of the sterilizing solution and also reduces the operating cost of the cleaning apparatus. It also eliminates the need for a frequent recharging of the sterilizing solution. The sterilizing step is preceded and followed by a quiescent interval, thereby preventing dilution of the sterilizing solution. The sterilizing step is also preceded by a water rinse step, which prevents the sterilizing solution from being contaminated by coeliac fluid, blood or other contaminants which remain attached to the distal end or inner end of the endoscope, allowing the sterilizing solution to be effective over an increased period of time.

DESCRIPTION OF THE PREFERRED EMBODIMENT

Figure 1:
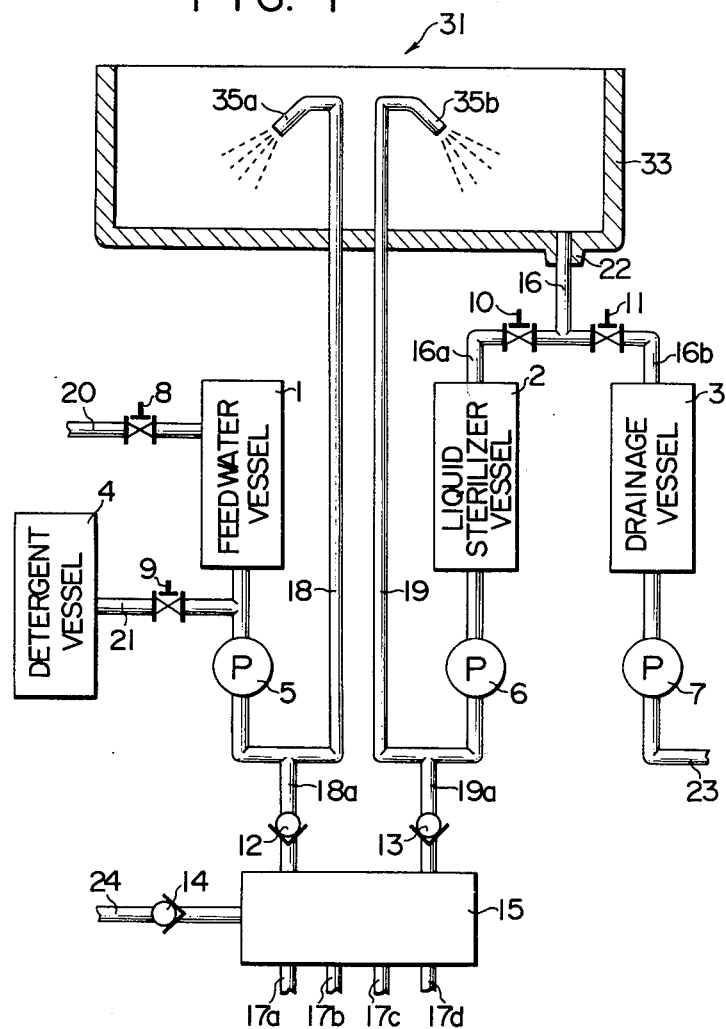
FIG. 1 is a schematic diagram of an apparatus for cleaning an endoscope which is used to carry out the method of the invention.

Referring to FIG. 1, there is shown a cleaning apparatus according to the invention which is generally indicated by numeral 31. Essentially, it comprises four liquid-containing vessels including feedwater vessel 1, liquid sterilizer vessel 2, drainage vessel 3 and detergent vessel 4; three pumps including cleaning water feed pump 5, liquid sterilizer feed pump 6 and drain pump 7; four electromagnetic valves including feedwater valve 8, detergent valve 9, liquid sterilizer return valve 10 and drainage valve 11; header 15 for connection with the channels of an endoscope; three check valves including check valve 12 for supplying cleaning water, check valve 13 for supplying liquid sterilizer and air check valve 14; rinse basin 33; and sprays 35a, 35b associated with a cleaning water and a liquid sterilizer, respectively.

Feedwater vessel 1 is connected with the faucet, not shown, of an available water service through conduit 20, with electromagnetic valve 8 interposed between vessel 1 and the faucet. Valve 8 is closed when a given quantity of cleaning water is stored in vessel 1, and is opened whenever the water supply of vessel 1 falls below another given level, thus maintaining a given quantity of water therein. Feedwater vessel 1 is connected with cleaning water spray 35a disposed within rinse basin 33 through water feed tube 18. The spray 35a may comprise a spray head. Feed pump 5 disposed in feed tube 18 is selectively operated to supply the cleaning water contained in feedwater vessel 1 to spray 35a. Between feedwater vessel 1 and pump 5, feed tube 18 is connected with detergent vessel 4 through feed tube 21 which includes electromagnetic valve 9. By selectively operating valve 9, the supply of liquid detergent can be controlled.

Liquid sterilizer vessel 2 is connected through feed tube 19 with liquid sterilizer spray 35b which is disposed within rinse basin 33 and which may comprise a spray head, with feed pump 6 being connected in feed tube 19 to supply the liquid sterilizer from vessel 2 to spray 35b. Liquid sterilizing vessel 2 is also connected with return tube 16a which is in turn connected through electromagnetic valve 10 and drain tube 16 with drain port 22 of rinse basin 33.

Drainage vessel 3 is connected through drain tube 16b and electromagnetic valve 11 with drain tube 16 which is connected with drain port 22 of rinse basin 33. Thus, drain tube 16 is formed with a pair of branches, one of which is connected with return valve 10 and the other end of which is connected with drain valve 11. Drainage vessel 3 is also connected with drain tube 23 in which drain pump 7 is connected. Pump 7 may be selectively operated to discharge the used cleaning liquid out of drainage vessel 3.

Header 15 is connected with cleaning water feed tube 18a which branches off from feed tube 18 and which has check valve 12 connected therein, valve 12 allowing a flow of the cleaning water or liquid detergent as fed by pump 5 from vessel 1 or 4 in only one direction, namely, toward header 15. Header 15 is also connected with liquid sterilizer feed tube 19a which branches off from feed tube 19 and which has check valve 13 connected therein, valve 13 allowing a flow of liquid sterilizer as supplied from vessel 2 by pump 6 only in one direction, namely, toward header 15. Additionally, header 15 is also connected with an air delivery unit, not shown, through air feed tube 24 in which air check valve 14 is connected to control the supply of air to header 15.

Also connected with header 15 is a plurality of tubes 17a to 17d which supply cleaning water, a detergent solution, a liquid sterilizer or air to a forceps channel, an air channel, a liquid feed channel and a suction channel of an endoscope, respectively. These tubes 17a to 17d are adapted to be connected with the openings of the individual channels disposed in the operating end of the endoscope. Feed tubes 18a, 19a, 24 communicate with tubes 17a to 17d in a manner such that the cleaning water, detergent solution, liquid sterilizer and air supplied through tubes 18a, 19a, 24 can be delivered into the respective channels through tubes 17a to 17d.

Figure 2:
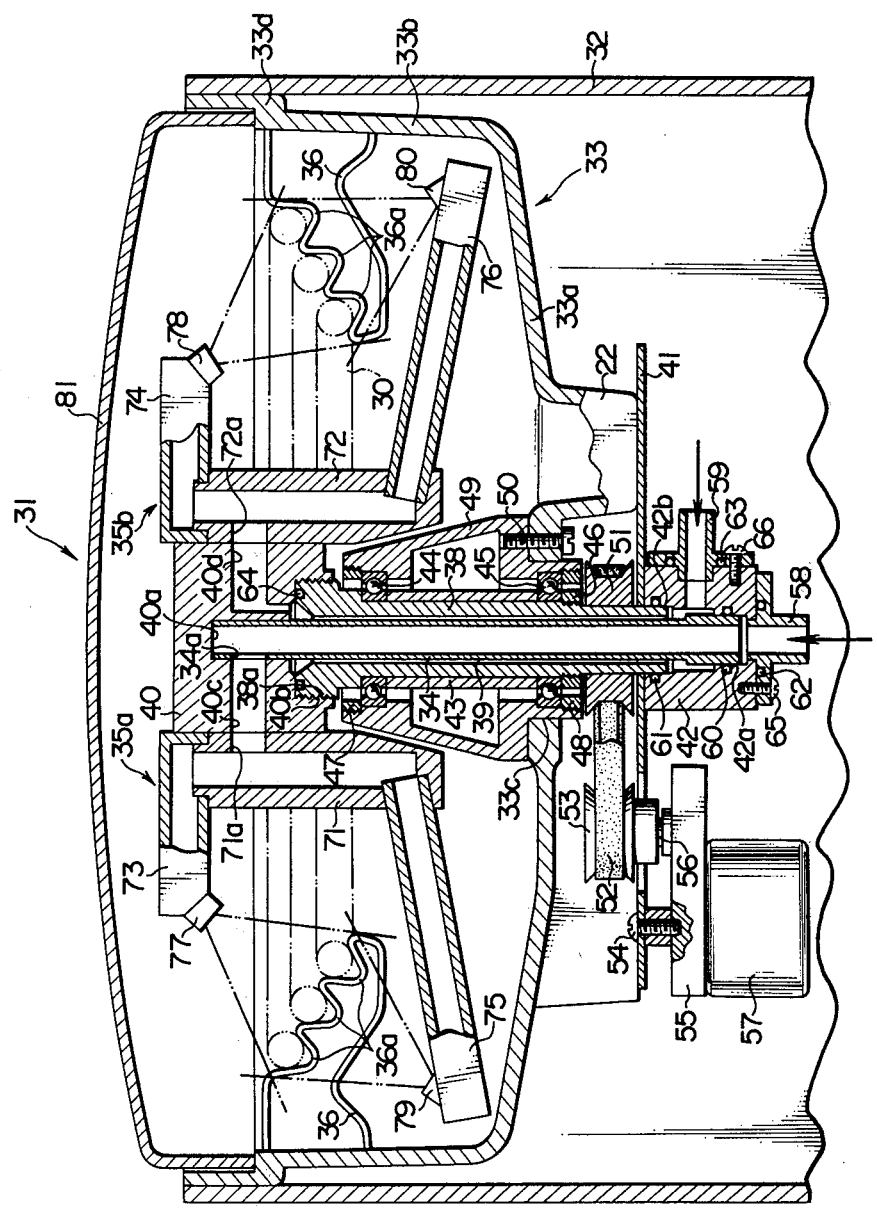
FIG. 2 is a fragmentary longitudinal section, illustrating a specific arrangement of a cleaning apparatus shown in FIG. 1.

FIG. 2 shows a specific construction of cleaning apparatus 31. Specifically, apparatus 31 comprises cylindrical rinse basin 33 having bottomplate 33a and which is fitted into and secured to the upper end of cylindrical frame 32 which defines the outer wall of the apparatus. Bottomplate 33a is centrally formed with opening 33c through which extends hollow liquid feed, shaft 34 which is rotatable relative to rinse basin 33. Hollow drive shaft 38 is rotatably disposed around hollow shaft 34 and defines gap 39 therebetween. Drive shaft 38 also serves supplying a liquid. Liquid feed path forming member 40 is secured to the top end of shaft 34, and defines a plurality of liquid feed paths which are connected with liquid feed tubes 73 to 76 secured thereto. A pair of cleaning liquid spray heads 77, 79 and a pair of liquid sterilizer spray heads 78, 80 are mounted on the free end of respective liquid feed tubes 73 to 76. A plurality of support members 36 have their opposite ends secured to inner cylindrical wall 33b of rinse basin 33 and extend toward the center of basin 33, these support members being adapted to carry a distal end or an inner end of the endoscope thereon.

Hollow liquid feed, hollow shaft 34 is loosely fitted into hollow shaft 38 to form gap 39 therebetween, as mentioned previously, and has its upper end fitted into cylindrical hole 40a formed in square pillar-shaped, liquid feed path forming member 40. The lower end of shaft 34 is rotatably fitted into central bore 42a of coupler mount 42 which is integrally secured to the underside of support plate 41 which is in turn fixedly mounted on a stationary member of apparatus 31. O-ring 60 is interposed between the lower end of shaft 38 and the wall which defines bore 42a. The upper end of hollow shaft 38 is peripherally formed with threads 38a which are engaged by threads 40b formed on member 40, with O-ring 64 interposed between the upper end of hollow shaft 38 and member 40. The lower end of hollow shaft 38 is rotatably fitted into central bore 42b formed in coupler mount 42, with O-ring 61 interposed therebetween.

Intermediate its length, hollow shaft 38 is peripherally provided with cylindrical distance piece 43, the upper and lower ends of which fixedly carry the inner races of bearings 44, 45, the outer races of which are secured to bearing frame 49 by means of nuts 46, 47, 48, whereby hollow shaft 38 is rotatably supported by frame 49. Frame 49 is in the form of a truncated cone through which shafts 34 and 38 extend, and has its lower end secured within central bore 33c formed in rinse basin 38, by means of set screw 50. In a region projecting downwardly through frame 49, drive shaft 38 fixedly carries drive pulley 51, which is coupled through belt 52 with output pulley 53 which is in turn fixedly mounted on drive shaft 56 extending upwardly from gear box 55, secured to support plate 41 by means of set screw 54. Drive shaft 56 is connected with the output shaft of drive motor 57 through a reduction gearing located within gear box 55. It is to be understood that motor 57 is energized whenever feed pumps 5, 6 (see FIG. 1) associated with the supply of the cleaning water and the liquid sterilizer are operated.

Feedwater fitting 58 is disposed on the underside of coupler mount 42 and secured thereto by screw 65, with O-ring 62 interposed therebetween. Fitting 48 communicates with the interior of liquid feed shaft 34. Similarly, fitting 59 which is adapted to supply a liquid sterilizer is disposed in abutment against a side of coupler mount 42, and communicates with gap 39 defined between shafts 34, 38. Fitting 49 is secured to coupler mount 42 by set screw 66, with O-ring 63 interposed therebetween. These fittings 58, 59 are connected with feed tubes 18, 19 (see FIG. 1), respectively. In this manner, the interior of shaft 34 represents a feedwater path while gap 39 defined between shafts 34, 38 represents a liquid sterilizer supply path. It will be appreciated that O-rings 60 to 64 are effective in preventing the leakage and the admixture of a cleaning water and a liquid sterilizer.

Adjacent to its upper end, liquid feed shaft 34 has opening 34a formed in its sidewall, which communicates with water feed path 40c formed in member 40. Member 40 is also formed with liquid feed path 40d which communicates with gap 29 defined between shafts 34, 38. It will be noted that these paths 30c, 30d communicate with openings 71a, 72a, respectively, which are formed in the sidewall of liquid feed tube mounting members 71, 72 which are fixedly mounted on the sidewall of member 40.

Mounting members 71, 72 comprise elongate pipes which have their upper end connected with horizontally and radially extending liquid feed tubes 73, 74, each having a relatively small length. The lower ends of mounting members 71, 72 are connected with liquid feed tubes 75, 76 having a relatively great length and which extend both radially and slightly downward. Upper spray heads 77, 78 are mounted on the free end of liquid feed tubes 73, 74 in a downward and outward orientation while lower spray heads 79, 80 are mounted on the free end of liquid feed tubes 75, 76 in an upward and inward orientation. Upper spray head 77 and lower spray head 79 are located opposite to each other as are upper spray head 78 and lower spray head 80. A slit-shaped spray aperture (not shown) which has a given angle of inclination with respect to the axis of the associated liquid feed tubes 73 to 76 is formed in that surface of each spray head 77 to 80 which opposes the other spray head. Consequently, the cleaning liquid and liquid sterilizer supplied to spray heads 70 to 78 are sprayed through the aperture therein while spreading as indicated by phantom line in FIG. 2.

Support members 36 mentioned above extend into positions intermediate the oppositely located spray heads 77 and 79 or 78 and 80 in order to receive the distal end or inner portion 30 of the endoscope which has been inserted into the coeloma, at a cleaning position. These support members 36 are formed of metal wires which are folded to define a plurality of depressions 36a in which the successive turns of the endoscope portion 30 are received. The opposite ends of support members 36 are secured to cylindrical wall 33b of rinse basin 33. It will be appreciated that the endoscope portion 30 is spirally disposed on depressions 36a of support members 36.

Mounting member 71, liquid feed tubes 73, 75 and spray heads 77, 79 constitute together cleaning water spray 35a shown in FIG. 1 while mounting member 72, liquid feed tubes 74, 76 and spray heads 78, 80 constitute together liquid sterilizer spray 35b also shown in FIG. 1. Since these sprays 35a, 35b are fixedly mounted on hollow drive shaft 38 with member 40 interposed therebetween, they are driven for rotation about the axis of hollow shaft 38 whenever motor 57 is energized at the same time as pumps 5, 6 are operated in order to move the sprays over successive lengths of the endoscope portion 30 which is spirally disposed on support members 36. Thus spray heads 77, 79 or 78, 80 spray a cleaning liquid or a liquid sterilizer while rotating to clean or sterilize the successive lengths of the outer surface of the endoscope portion 30. One revolution of spray heads 77 to 80 is effective to clean or sterilize the entire length of the endoscope portion 30 completely.

In FIG. 2, numeral 81 represents a top cover of apparatus 31 which bears against step 33d formed on cylindrical wall 33b of rinse basin 33. Numeral 22 represents a drain port which is connected with drain tube 16 (see FIG. 1).

The operation of cleaning apparatus 31 will now be described by means of three examples, using cleaning water, a detergent solution and a sterilizing solution. It is assumed that the endoscope portion 30 is already disposed in place on support members 36, and that the tubes 17a to 17d extending from header 15 are connected with the openings of respective channels located in the operating end of the endoscope.

1. Cleaning with water

In this instance, return valve 10 is closed while drain valve 11 is opened. As feed pump 5 is operated, the water contained in feedwater vessel 1 is supplied through feed tube 18 to be sprayed by spray 35a, thus cleaning the endoscope portion 30. Simultaneously, the water from vessel 1 is also supplied to header 15 through feed tube 18a, whereby it is supplied to the individual channels of the endoscope through tubes 17a, 17d, thus cleaning the interior of the respective channels.

The water sprayed by spray 35a as well as the water fed into and passing through the respective channels of the endoscope flows into rinse basin 33, and thence to drainage vessel 3 through a path including drain port 22, drain tube 16, valve 11 and drain tube 16b. By operating drain pump 7, the water collected can be discharged out of apparatus 31 through drain tube 23.

2. Cleaning with a detergent solution

Again, return valve 10 is closed while drain valve 11 is opened. When valve 9 is opened, and feed pump 5 is operated, a reduction in the pressure of pump 5 causes the liquid detergent contained in vessel 4 to be mixed with the water from vessel 1, and the mixture is supplied to spray 35a and to header 15. Subsequently, the liquid mixture is used to clean the outer surface of the endoscope portion 30 and the interior of the respective channels, and then discharged out of apparatus 31.

3. Sterilization with a liquid sterilizer

In this instance, valve 10 is opened while drain valve 11 is closed. As feed pump 6 is operated, the liquid sterilizer contained in vessel 2 is supplied through feed tube 19 to spray 35b, which sprays it to clean and sterilize the endoscope portion 30. At the same time, the liquid sterilizer from vessel 2 is also supplied to header 15 through feed tube 19a, and thence supplied to the interior of the respective channels of the endoscope through tubes 17a to 17d, thus sterilizing the individual channels. Subsequently, the liquid sterilizer sprayed by spray 35b and the liquid sterilizer which have passed through the interior of the respective channels of the endoscope reflow to vessel 2 to be stored therein, through a path including drain port 22, drain tube 16, valve 10 and return tube 16a.

After the endoscope portion 30 has been cleaned and sterilized in this manner, air for drying is supplied from a ventilator through header 15 to be fed into the respective channels, thus drying the inside thereof. It will be understood that the outer surface of the endoscope portion 30 can be naturally dried.

Figure 3:
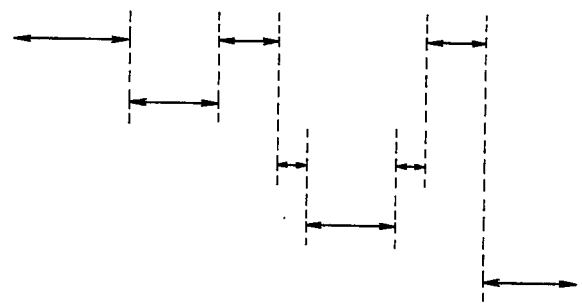
FIG. 3 is a chart illustrating the various steps of a cleaning operation which is achieved with the apparatus shown in FIG. 1.

From the foregoing description, it will be appreciated that mixture of the cleaning water with the liquid sterilizer, which would dilute the latter, can be avoided and a return of the liquid sterilizer to vessel 2 can be achieved by controlling pumps 5 to 7 and valves 9 to 11 in a sequence of steps (A) to (H) shown in the table below. The resulting procedure is visualized in the chart of FIG. 3. This prevents any reduction in the concentration of the liquid sterilizer while assuring its conservation for reuse.

TABLE

|   |   | Pump 5 | Pump 6 | Pump 7 | Valve 9 | Valve 10 | Valve 11 |
|---|---|---|---|---|---|---|---|
| (A) | Water cleaning | operated | inoperative | operated | closed | closed | open |
| (B) | Cleaning with detergent solution | operated | inoperative | operated | open | closed | open |
| (C) | Water cleaning (fixed time | operated | inoperative | operated | closed | closed | open |

TABLE-continued

|     |                                    | Pump 5      | Pump 6      | Pump 7      | Valve 9 | Valve 10 | Valve 11 |
|-----|------------------------------------|-------------|-------------|-------------|---------|----------|----------|
|     | interval)                          |             |             |             |         |          |          |
| (D) | Quiescent period                   | inoperative | inoperative | operated    | closed  | closed   | open     |
| (E) | Sterilization                      | inoperative | operated    | inoperative | closed  | open     | closed   |
| (F) | Quiescent period                   | inoperative | inoperative | inoperative | closed  | open     | closed   |
| (G) | Water cleaning (fixed time interval) | operated  | inoperative | operated    | closed  | closed   | open     |
| (H) | Drying                             | inoperative | inoperative | operated    | closed  | closed   | closed   |

Specifically, pumps 5 and 7 are initially operated to effect the water cleaning step (A), followed by the opening of valve 9 to effect the cleaning step (B) with a detergent solution. At the time the cleaning step (B) is terminated, any coeliac fluid, blood or contaminants which may remain on the endoscope portion 30 are completely flushed away. Then, the water cleaning step (C) is performed in order to remove any detergent solution which remains on the endoscope portion 30 as a result of the cleaning step (B). Since the purpose of the cleaning step (C) is to remove any residue of detergent, it may be operated for a given duration. Subsequently, pump 5 is rendered inoperative to provide a quiescent period (D). The purpose of the quiescent period (D) is to provide a sufficient time interval to allow the cleaning water which is used in the cleaning step (C) to be completely discharged from within rinse basin 33 and drain tube 16 in order to prevent any mixture thereof with the liquid sterilizer during the next sterilization step (E). Valve 10 which has been maintained closed is now opened while valve 11 is closed, and pump 6 is operated to perform the sterilization step (E). During the sterilization step (E), the liquid sterilizer returns to vessel 2. Thereafter, the operation of pump 6 is interrupted, providing another quiescent period (F). Again, the purpose of quiescent period (F) is to allow the liquid sterilizer used during the sterilization step (E) to be completely displaced from the interior of rinse basin 33 and drain tube 16 and returned to vessel 2, thus preventing its mixture with the cleaning water which is used in the following water cleaning step (G). Valve 10 is now closed while valve 11 is opened, and pump 5 is operated to effect the water cleaning step (G). The purpose of the cleaning step (G) is to flush away any residue of liquid sterilizer which may be attaching to the endoscope portion 30 as a result of the sterilization step (F). Accordingly, the duration of this step (G) may be preset. Subsequently, the operation of pump 5 is interrupted, and a ventilator (not shown) is operated to feed drying air into the individual channels of the endoscope through header 15 to effect the drying step (H). This completes the cleaning operation for the endoscope.

It will be readily appreciated that the sequence of cleaning steps mentioned above can be pre-programmed using well-known electrical circuit means, thereby allowing a completely automatic control of the cleaning apparatus. Also, it should be noted that the described cleaning steps are exemplary only, and additional steps may be included or some of the described steps may be omitted as required. The present invention may be embodied in other specific forms without departing from the spirit or essential attributes thereof, and accordingly, reference should be made to the appended claims, rather than to the foregoing specification as indicating the scope of the invention.

What is claimed is:
1. An apparatus for cleaning an endoscope, comprising:
   rinse basin means adapted to receive a portion of an endoscope to be cleaned, said rinse basin means including a first spray head means for spraying a cleaning liquid and a second spray head means for spraying a liquid sterilizer;
   drain means formed in said rinse basin means;
   a first feed pump for supplying said cleaning liquid to said first spray head means;
   a second feed pump for supplying said liquid sterilizer to said second spray head means from a vessel containing a quantity of said liquid sterilizer;
   a drain tube means connected with said drain means and having first and second branches;
   a return tube means connected with said first branch and communicating with said vessel via a first electromagnetic valve which is operable when a return of said liquid sterilizer to said vessel is desired;
   second drain tube means connected with said second branch and including a second electromagnetic valve which is operable when drainage of a liquid from said rinse basin means is desired; and
   header means cooperating with said first and second feed pumps to feed at least one of the group of water, liquid detergent and liquid sterilizer into individual channels of an endoscope located in said rinse basin means so that such fluid passes through the endoscope, is discharged into said rinse basin means and is recirculated through said apparatus via said drain means.

2. An apparatus according to claim 1 wherein said header means also cooperates with an air ventilator which, when operated, supplies air into said channels of said endoscope for drying each of said channels after the completion of a cleaning operation.

3. An apparatus according to either of claims 1 or 2, wherein said cleaning liquid is water.

4. An apparatus according to either of claims 1 or 2, wherein said cleaning liquid is a liquid detergent.

5. An apparatus according to claim 1, further comprising control means for controlling the operation of said feed pumps and of said valves.

6. An apparatus according to claim 5, wherein said control means is adapted to operate said feed pumps and said valves in a predetermined order and with a predetermined timing.

7. An apparatus according to claim 6, wherein said control means is adapted to operate said feed pumps and said valves in such a manner as to cause both said feed pumps to be inactive for a predetermined quiescent period after each introduction of either of said fluids into either of said spray heads or into said header means.

* * * * *